US006460542B1

(12) United States Patent
James

(10) Patent No.: US 6,460,542 B1
(45) Date of Patent: Oct. 8, 2002

(54) FEMALE INCONTINENCE CONTROL DEVICE

(75) Inventor: Larry W. James, 1072 NW. High Point Dr., Lee's Summit, MO (US) 64081

(73) Assignees: Medical Technology & Innovations, Inc., Riviera Beach, FL (US); Larry W. James, Lee's Summit, MO (US)

( * ) Notice: Subject to any disclaimer, the term of this patent is extended or adjusted under 35 U.S.C. 154(b) by 0 days.

(21) Appl. No.: 09/753,511

(22) Filed: Jan. 3, 2001

(51) Int. Cl.$^7$ .................................................. A61F 5/48
(52) U.S. Cl. ............................... 128/885; 128/DIG. 25; 600/29
(58) Field of Search ................................ 128/846, 885, 128/886, DIG. 25; 600/29–31

(56) References Cited

U.S. PATENT DOCUMENTS

| | | |
|---|---|---|
| 3,554,184 | 1/1971 | Habib |
| 4,139,006 | 2/1979 | Corey |
| 4,669,478 | 6/1987 | Robertson |
| 4,749,186 | * 6/1988 | Harding-Randle ... 128/DIG. 25 |
| 4,822,333 | * 4/1989 | Lavarenne ........... 128/DIG. 25 |
| 4,920,986 | 5/1990 | Biswas |
| 5,007,894 | 4/1991 | Enhorning |
| 5,036,867 | 8/1991 | Biswas |
| 5,386,836 | 2/1995 | Biswas |
| 5,755,236 | 5/1998 | Dann et al. |
| 5,771,899 | 6/1998 | Martelly et al. |
| 5,785,640 | 7/1998 | Kresch et al. |
| 5,840,011 | 11/1998 | Landgrebe et al. |

FOREIGN PATENT DOCUMENTS

| | | | | |
|---|---|---|---|---|
| DE | 2600259 | * | 1/1975 | .......... 128/DIG. 25 |
| DE | 2747245 | * | 4/1979 | .......... 128/DIG. 25 |

OTHER PUBLICATIONS

Urodynamic outcome after surgery for severe prolapse and potential stress incontinence by John James Klutke, MD, and Susanne Ramos, MD, Los Angeles, California; from the University of Southern California School of Medicine, Department of Obstetrics and Gynecology.
Sexual function and vaginal anatomy in women before and after surgery for pelvic organ prolapse and urinary incontinence by Anne M. Weber, MD, Mark D. Walters, MD, and Marion R. Piedmonte, MA, Cleveland, Ohio; from the Department of Gynecology and Obstetrics and the Department of Biostatistics and Epidemiology, Cleveland Clinic Foundation.
A Survey of Pessary Use by Members of the American Urogynecologic Society by Geoffrey W. Cundiff, MD, Alison C. Weidner, MD, Anthony G. Visco, MD, Richard C. Bump, MD, and W. Allen Addison, MD; from the Department of Obstetrics and Gynecology, Duke University Medical Center, Durham, North Carolina.
Rosen Inflatable Urinary Incontinence Prothesis, Jul. 1978.*

* cited by examiner

Primary Examiner—Michael A. Brown
(74) Attorney, Agent, or Firm—Shughart Thomson & Kilroy P.C.; Marcia J. Rodgers

(57) ABSTRACT

A female incontinence device and method for placement of an intravaginal device for repositioning and supporting the prolapsed neck of the urinary bladder and realigning the urethra both vertically and laterally to approximate normal anatomical position enable a patient to remain stress-continent. The device includes an open, generally droplet-shaped base coupled with a pair of elongate spaced parallel legs shaped to extend in orthogonal relationship to the plane of the base in a predetermined configuration. Upon installation, the legs provide support for the anterior wall of the vagina and adjacent neck of the urinary bladder at a preconfigured variable distance from the posterior vaginal wall, as well as lateral and vertical alignment and support of the adjacent urethra. Alternatively, the base may be coupled with a single leg having a predetermined configuration which extends orthogonal to the plane of the base and is attached to the base at both ends.

18 Claims, 6 Drawing Sheets

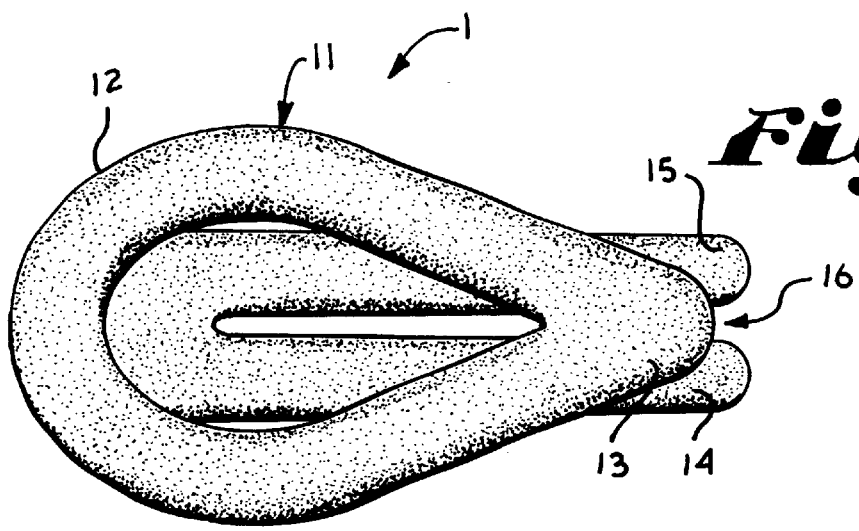
Fig. 4.
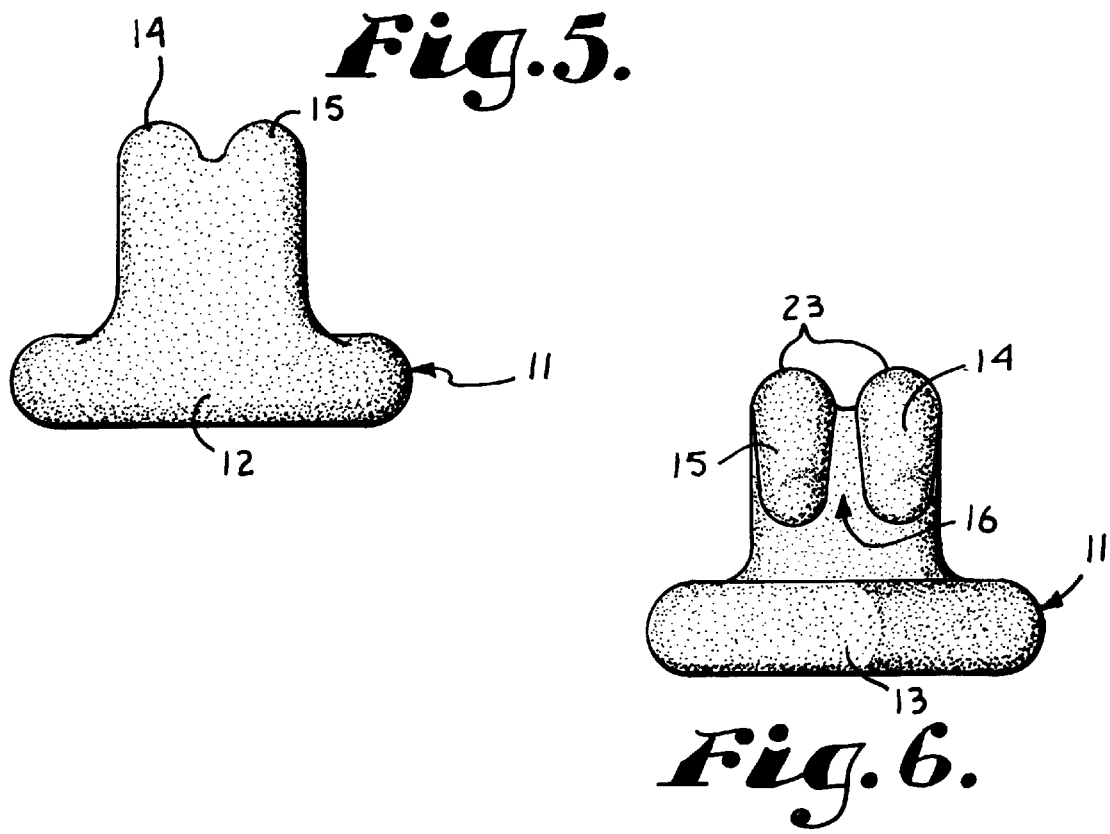
Fig. 5.
Fig. 6.

FEMALE INCONTINENCE CONTROL DEVICE

The present invention is broadly concerned with an apparatus and method for controlling urinary incontinence in human females. More particularly, it is directed to a prosthesis which can be inserted intravaginally to reposition and support the urinary bladder.

Urinary incontinence (UI), or involuntary loss of urine from the bladder, is prevalent among adult women. According to the Agency for Health Care research and Quality of the Department of Health and Human services, more than 11 million American women suffer from some form of urinary incontinence. More than $16 billion is spent every year in the United States on incontinence related care. UI is more common in women because pregnancy and childbirth may weaken the bladder supporting muscles in the pelvic floor and cause pelvic organ prolapse. It is also more prevalent in postmenopausal women, who have lower blood levels of estrogen, which helps to maintain muscle tone around the urethra. There are four primary types of UI: stress, functional, urge and overflow incontinence.

Stress incontinence occurs when the urethra fails to keep the neck of the bladder closed during exertion. It occurs during sudden increases in intra-abdominal pressure, for example, during physical exertion, lifting, laughing, coughing and sneezing. Urge incontinence, also known as "overactive bladder", is the result of involuntary contractions of the detrusor muscle. Functional incontinence is the result of impaired mobility or mental function, which may arise for example, secondary to Alzheimer's disease. Overflow incontinence is the result of weak bladder muscles, which may arise for example, secondary to nerve damage, or blockage of the urethra. Stress and urge incontinence are most common in women, and often occur together as so-called "mixed" incontinence.

Therapeutic treatment of UI in women varies according to type. Functional incontinence is treated by addressing the underlying impairment, if possible. Overflow incontinence is rare in women. While urge incontinence may be treated by anticholinergic drugs, these drugs are not effective in treating stress incontinence.

Stress incontinence is caused by loss of muscular support to the urethra and neck of the bladder. It may be treated surgically, by rehabilitation of the pelvic muscles, and by use of prosthetic devices, known as pessaries, which are inserted into the vagina to support the prolapsed neck of the bladder and urethra. Prosthetic devices are particularly suitable for use by patients who are not surgical candidates or who decline surgery.

Previous prosthetic devices have attempted to achieve normal bladder support by applying pressure to the anterior wall of the vagina and adjacent neck of the bladder and urethra. Such anterior pressure does not provide lateral alignment of the urethra and may serve to exacerbate any lateral urethral deviation. Moreover, when such a device exerts pressure on the tissue in excess of 32 mm Hg, the capillaries close, cutting off the cellular blood supply and eventually resulting in necrosis of the adjacent tissue, manifested as vaginal pressure ulcers. Even where such devices do not damage the tissue by exerting excessive pressure, the pressure they do cause results in occlusion of the urethra, setting up a local irritation and attendant patient discomfort. An increase in the incidence of urinary tract infections has been reported in patients who use such prosthetic devices for extended periods of time.

Known intravaginal support devices are of two general types. So-called support pessaries are generally ring shaped, and are retained in place by the pubic bone to exert a spring action against the anterior vaginal wall. So-called space-filling pessaries are held in place by their size or by a suction action against the vaginal walls. There is a need for an intravaginal prosthetic support device or pessary which will align the urethra and reposition and support the bladder in a normal anatomical position. There is also a need for such a support device which does not occlude the urethra or exert excessive pressure on the surrounding tissues.

The apparatus of the present invention is specifically designed to provide an intravaginal prosthetic device which can support the urinary bladder and align the urethra in correct anatomical position without discomfort or excessive pressure on the urethra or surrounding tissues.

SUMMARY OF THE INVENTION

The present invention is directed to a female incontinence device and method for placement of an intravaginal device for repositioning and supporting the prolapsed neck of the urinary bladder and realigning the urethra both vertically and laterally to achieve normal anatomical position enabling a patient to remain stress-continent. The incontinence device of the present invention includes an open, generally droplet-shaped base coupled with a pair of elongate spaced parallel legs shaped to extend in a predetermined configuration in orthogonal relationship to the plane of the base. Upon installation in the vaginal canal, the legs provide support for the anterior wall of the vagina and adjacent neck of the urinary bladder at a preconfigured variable distance from the posterior vaginal wall, as well as lateral and vertical alignment and support of the adjacent urethra. Alternatively, the base may be coupled with a single leg having a predetermined configuration and extending orthogonal to the plane of the base and attached to the base at both ends.

OBJECTS AND ADVANTAGES OF THE INVENTION

The principal objects of the present invention are: to provide an improved apparatus and method for controlling urinary incontinence in women; to provide such an apparatus and method for repositioning and providing lateral and subjacent support to the neck of the bladder and the urethra; to provide such an apparatus and method for supporting the bladder and urethra while providing a templet for lateral alignment of the urethra; to provide such an apparatus and method for supporting the bladder and urethra while correcting the lateral alignment of the urethra; to provide such an apparatus which does not occlude the urethra; to provide such an apparatus which does not require flexed positioning behind the pubic bone to remain in place; to provide such an apparatus which may be positioned manually without surgical intervention; to provide such an apparatus which is available in an array of sizes so that an appropriate size can be selected to fit the pelvic anatomy of a patient; providing such an apparatus which can be easily installed and removed by a patient without assistance; to provide such an apparatus having a pair of spaced parallel legs for receiving and aligning an adjacent urethra therebetween; to provide a method for inserting such an apparatus intravaginally, positioning the device so that the superior aspects of the legs reposition and support the prolapsed neck of a urinary bladder and the legs laterally align and support the urethra for controlling urinary incontinence in women, and permitting the device to remain in place for an extended period of time; providing such an apparatus and method which are relatively easy to use, inexpensive to produce and particularly well-suited for their intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

BRIEF DESCRIPTION OF THE DRAWINGS

FIG. 4 is a bottom plan view of the device of FIG. 2.

FIG. 5 is a front elevational view of the apparatus depicted in FIG. 1.

FIG. 6 is a real elevational view of the device of FIG. 1.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 13:
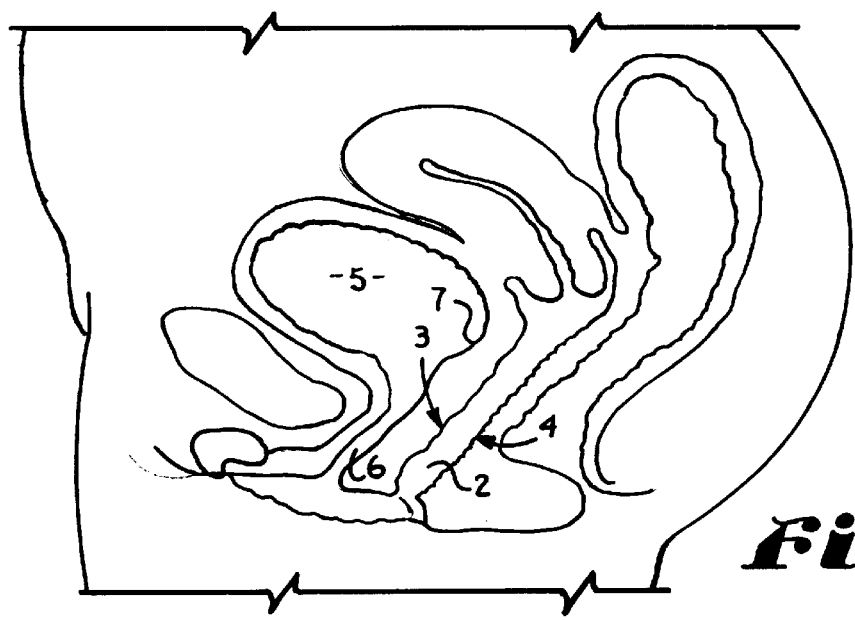
FIG. 13 is a sagittal sectional view of the female pelvic organs showing the organs in correct anatomical position.
Figure 14:
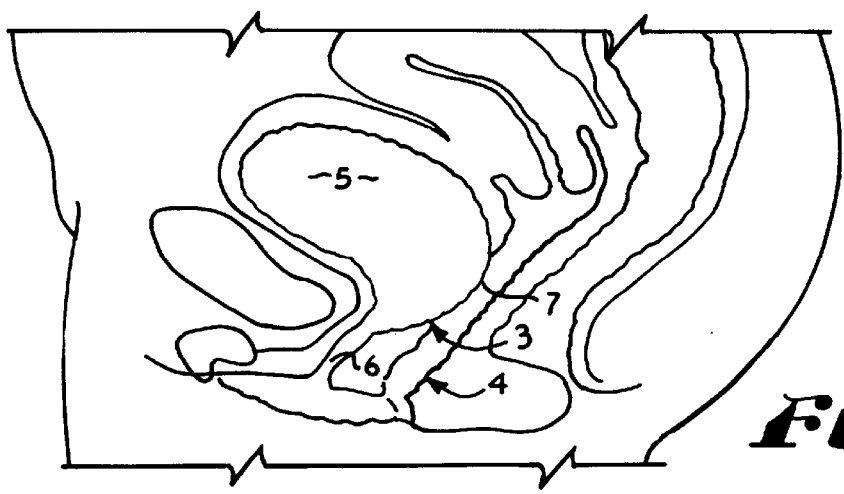
FIG. 14 is a sectional view similar to that depicted in FIG. 13, showing the urinary bladder prolapsed into the vaginal canal.
Figure 15:
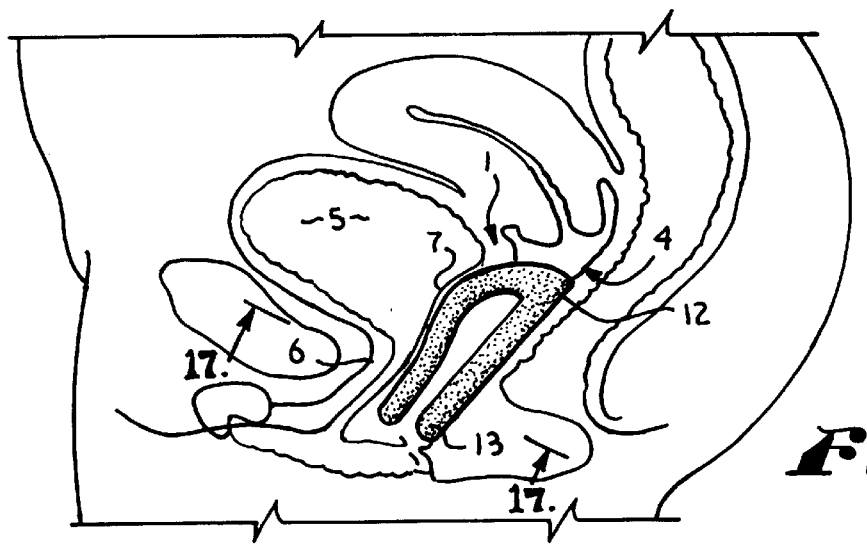
FIG. 15 is a sectional view similar to that depicted in FIG. 13, showing the device of FIG. 1 installed and illustrating repositioning and support of the neck of the urinary bladder and urethra.
Figure 16:
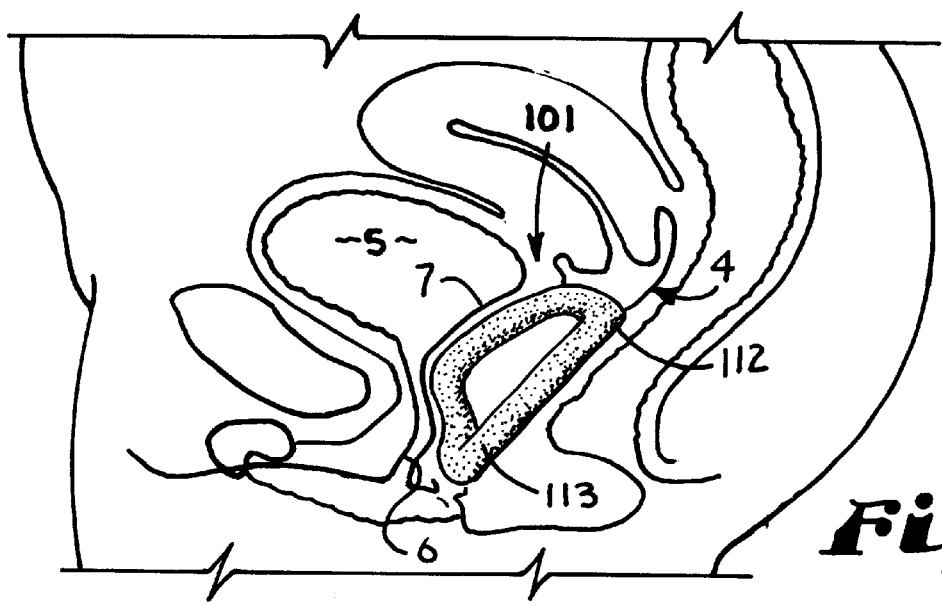
FIG. 16 is a view similar to FIG. 15 showing the device of FIG. 7 installed and illustrating repositioning and support f the urinary bladder and urethra.

Referring now to the drawings, a female incontinence control device is generally indicated by the reference numeral 1 and is depicted in FIGS. 1–6. FIGS. 13–15 illustrate a sagittal sectional view of the human female pelvic organs showing the vagina 2, which is the functional location of installation of the incontinence device 1, oriented between the anterior and posterior walls 3 and 4 and adjacent the bladder 5 and urethra 6, and in particular, adjacent the posterior wall 7 of the bladder 5.

As best shown in FIGS. 1–6, the incontinence device 1 broadly includes an open, droplet-shaped base 11, having an ellipsoid first end 12 which is positioned in a superior orientation during use and an approximately v-shaped convergent second end 13. During use, the second end 13 is positioned in an inferior orientation. A pair of elongate spaced legs 14 and 15 are coupled with the superior first end 12 of the base 11 in parallel relationship with a longitudinal space 16 therebetween. The legs 14 and 15 generally extend in parallel planes orthogonal to the plane of the base sw. The legs 14 and 15 are substantially identical, each having a first end 21 and a second end 22 with a central portion 23 therebetween. The leg first ends 21 are con joined adjacent to and coupled w ith the superior first end 12 of the base 11. The leg central portions 23 are shaped so that each leg forms an approximately S-shaped curve when viewed from the side. The unattached leg second ends 22 extend in spaced relationship to the plane of the base 11 and overlie the second end 13 of the base 11 slightly. The leg second ends 22 may be displaced toward the base 11 during deformation of the device 1 upon insertion. The distance between the legs 14 and 15 and the base 11 defines an eccentric space 24.

The central portion 23 of each leg 14 and 15 may be further described as comprising a superior portion 26 and an inferior portion 27. The superior portion 26 is curved outwardly from the base 11 and the inferior portion 27 is curved inwardly toward the base 11, so that overall the legs 14 and 15 have a generally s-shaped configuration when viewed in profile. The longitudinal space 16 between the legs 14 and 15 is sized and shaped to receive the urethra 6 and the adjacent portion of the anterior vaginal wall 3 and to form a template for lateral alignment of the urethra. The curvature of the central portion 23 of the legs 14 and 15 is adapted for supporting the anterior wall 3 of the vagina 2 and the adjacent prolapsed neck of the bladder 5 and the urethra 6 and maintaining them at a preconfigured variable distance from the posterior vaginal wall 4.

More specifically, the superior portion 26 of each leg 14 and 15 extends outwardly from the base 11 in spaced relationship for a predetermined distance designed to push the prolapsed neck of the bladder 5 away from the posterior wall 4 of the vagina 2 and to maintain the posterior wall 7 and neck of the bladder 5 in normal anatomical position. The curvature of the inferior portion 27 of each leg 14 and 15 is adapted to generally conform to and support the anterior vaginal wall 3 adjacent the urethra 6 in normal anatomical position without compressing or otherwise occluding the urethra 6.

In the preferred embodiment, the second ends 22 of the legs 14 and 15 are not connected to the base 11, permitting the second ends 22 to flex to a greater degree than the first ends 21. This increased capacity for flexion of the free second ends 22 reduces the likelihood that the inferior portion 27 of the legs 14 and 15 will compress the urethra 6, while maintaining sufficient rigidity of the superior portion 26 of the legs to maintain the posterior wall 7 of the bladder 5 in normal anatomical position.

The incontinence device 1 is of unitary construction and is preferably formed by molding an inert, biocompatible synthetic resin material having a modulus of elasticity such as, for example, a molded silicone compound or other suitable biocompatible material or combination of materials. In cross section, the base 11 and legs 14 and 15 are solid circular. The base has an outside length of about 25 to about 115 millimeters (mm), with a preferred length of about 95 mm and an outside width at the broadest point of about 25 to about 80 mm, with a preferred width of about 53 mm. The legs 14 and 15 extend in parallel planes orthogonal to the plane of the base 11 for about 40 to about 110 mm, with a preferred overall length of about 100 mm. The material forming the base 11 and legs 14 and 15 has a diameter of from about 5 to about 14 mm, with a preferred diameter of about 12.5 mm. At the closest point the interior surfaces of the legs 14 and 15 and the interior surface of the base 11 are spaced apart from about 5 mm to about 15, with a preferred spacing of about 10 mm.

The device 1 is depicted having an open, generally droplet-shaped base and a pair of spaced parallel legs with a generally s-shaped profile. Other suitable configurations may be employed. For example, the base 11 may be elliptical overall and it may be solid, filled, or webbed rather than open. Where a rectocele is present, such a solid, filled or webbed base configuration is particularly suitable for providing support to the posterior vaginal wall 4. The legs 14 and 15 may be joined by a web, attached to the base 11 at both ends 12 and 13, or a single wide leg may be provided which bifurcates adjacent the free end. The legs 14 and 15 may be constructed to present any suitable profile configuration for supporting the bladder and urethra, such as elliptical, rectangular or complex curvate. The shape of the legs 14 and 15 when viewed from the side may also be eccentric rather than symmetrical as depicted in the drawing figures.

In use, a device 1 having the correct size is selected for use by a patient in accordance with the dimensions of the vaginal canal 2. The patient grasps the device 1 and aligns it so that the base 11 faces posteriorly with the first end 12 in a superior orientation. In order to facilitate grasping and placement of the device, the inferior second leg ends 22 may be compressed against the lower end 13 of the base 11. The patient positions the device at the vaginal orifice and, using the posterior vaginal wall 4 as a guide, the device 1 is slidingly inserted into the canal 2 and urged upwardly until the legs 14 and 15 engage the anterior vaginal wall 3 adjacent the prolapsed neck of the bladder 5 and the lower end 13 of the base 11 and the inferior second ends 22 of the legs are positioned entirely within the canal 2. The elastomeric characteristics of the material permit deformation of the device 1 during insertion, but upon placement, the device assumes its molded shape.

Thus positioned, the incontinence device 1 of the present invention presents a generally s-shaped anterior profile with a planar rear profile when viewed from the side (FIGS. 2 and 15), with the legs 14 and 15 in parallel orientation so that the urethra is aligned within the space 16 between them and the neck of the bladder 5 is engaged and supported by the anteriorly curvate central portions 23.

Figure 17:
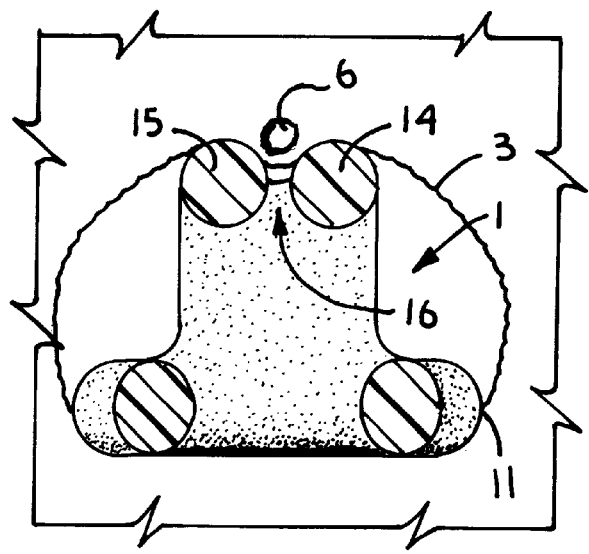
FIG. 17 is a diagrammatic, fragmentary cross-sectional view taken generally along line 17—17 of FIG. 15 showing the device 1 supporting a user's urethra.

If the first chosen device 1 does not comfortably provide the desired support of the bladder 5 and alignment of the urethra 6, then the device 1 is removed, an alternate device 1 of a larger or smaller size is selected and the process is repeated until the prolapsed neck of the bladder 5 is supported and the urethra is laterally aligned in the space 16 between the legs 14 and 15 of the device as generally shown in FIG. 17. The legs 14 and 15 are also adapted to flex separately in response to intra-abdominal torsional forces exerted thereon as the user moves.

Advantageously, the device 1 aligns and supports, but does not occlude the urethra 6, thus avoiding the morbidity normally associated with currently available devices. Maintained in place by the device 1, the bladder 5 functions normally, without regard to sudden increases in intra abdominal pressure resulting from exercise or other causes. In addition, because the bladder 5 is fully supported and the urethra 6 is aligned, voiding is complete, and no residual urine remains in a prolapsed area or cystocele to support bacterial growth which may result in infection.

The device 1 is installed manually, without the need for an applicator and is similarly removed for periodic cleaning by grasping the legs 14 and 15 and/or the lower end 13 of the base 11 and pulling outwardly through the vaginal canal 2.

While an exemplary configuration of an incontinence device having generally s-shaped legs 14 and 15 has been depicted, a wide variety of angles and variations on the configuration of the legs 14 and 15 may be employed to provide various degrees of posterior support to the bladder 5 and urethra 6.

The structure of a first modified embodiment of a female incontinence device in accordance with the invention is shown in FIGS. 7–12 and is generally represented by the reference numeral 101. The device 101 is similar to the embodiment previously described, except that a single leg is employed to support the adjacent bladder 5 and urethra 6 within the vagina 2 between the anterior and posterior walls 3 and 4.

Figure 1:
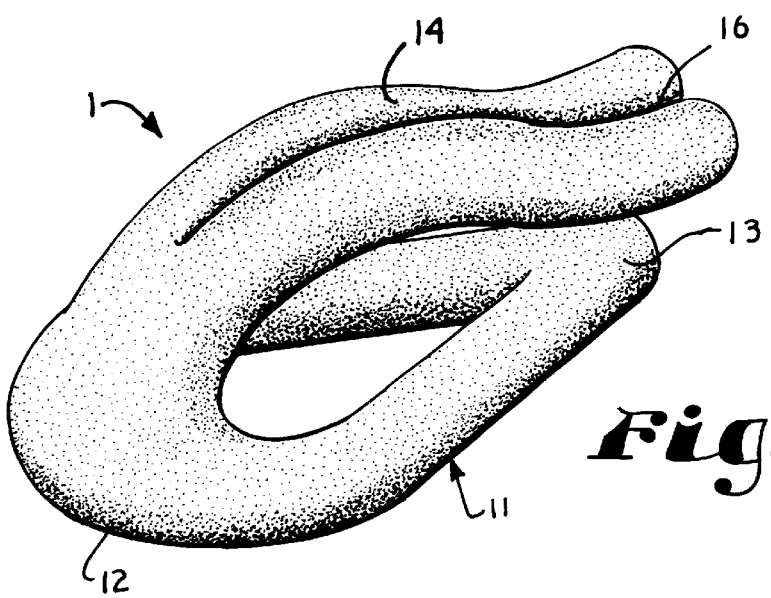
FIG. 1 is a perspective view of a female incontinence device.
Figure 2:
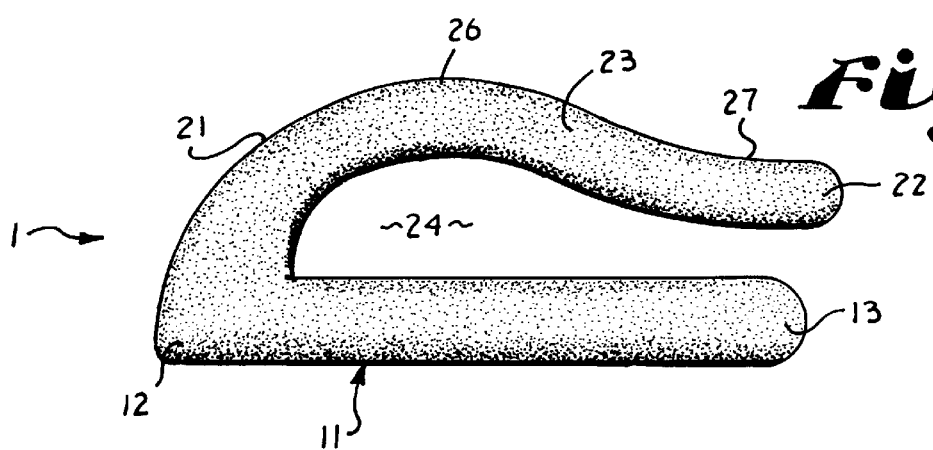
FIG. 2 is a side elevational view of the female incontinence device of FIG. 1 showing the legs extending a spaced distance in an orthogonal plane from the base.
Figure 3:
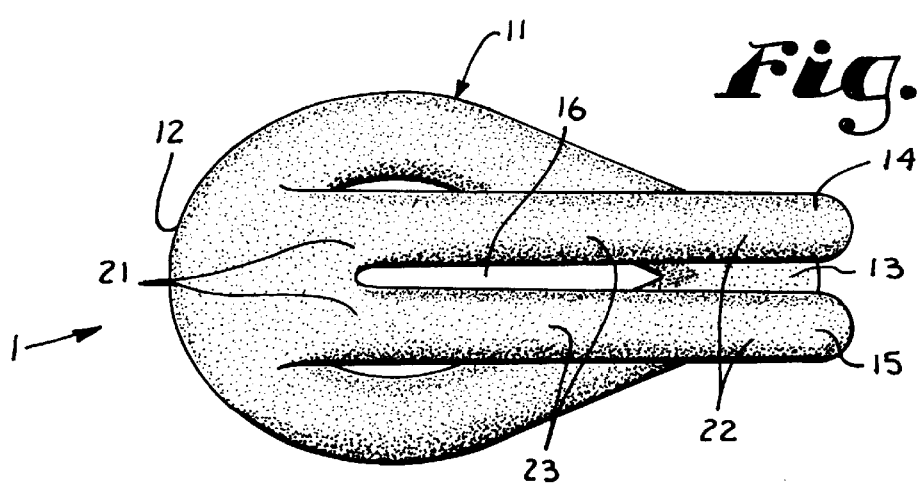
FIG. 3 is a top plan view of the device in FIG. 2, showing a longitudinal space between the legs.
Figure 7:
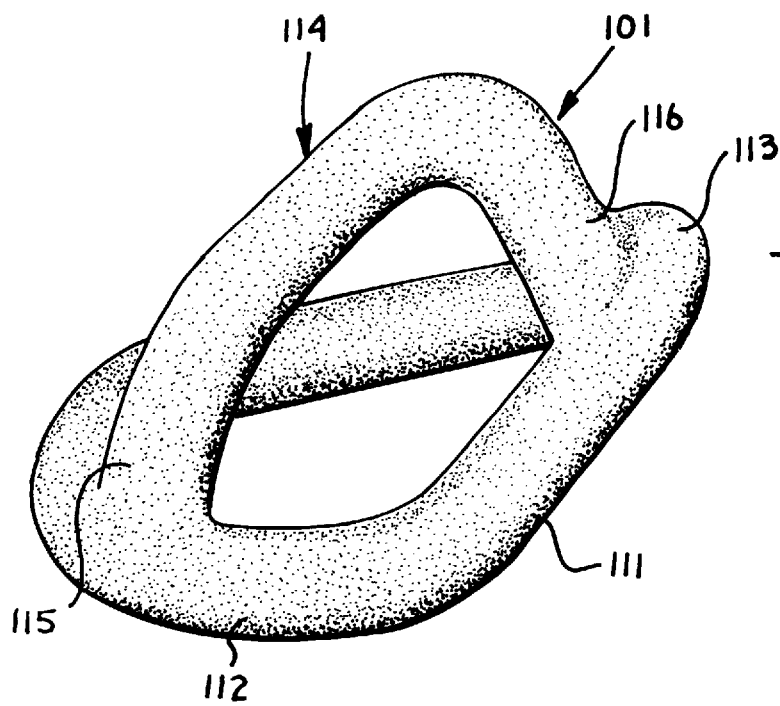
FIG. 7 is a perspective view of a first modified embodiment of the invention.
Figure 8:
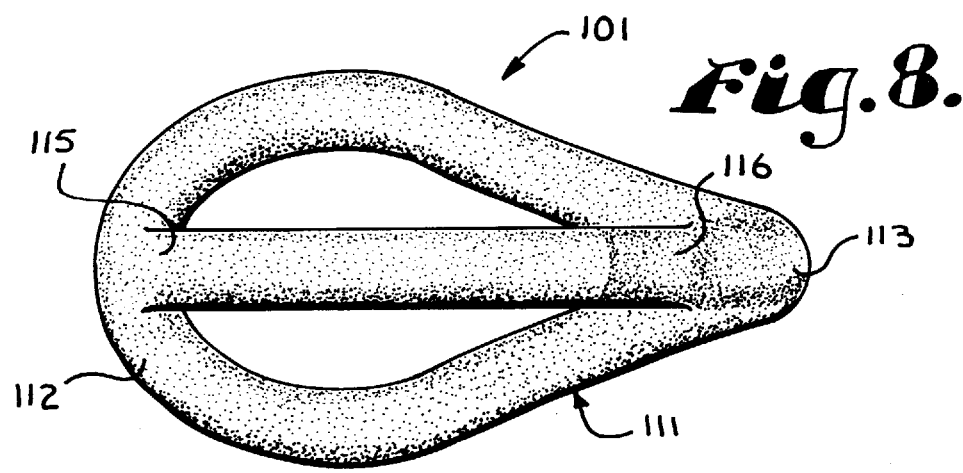
FIG. 8 is a top plan view of the embodiment depicted in FIG. 7.
Figure 9:
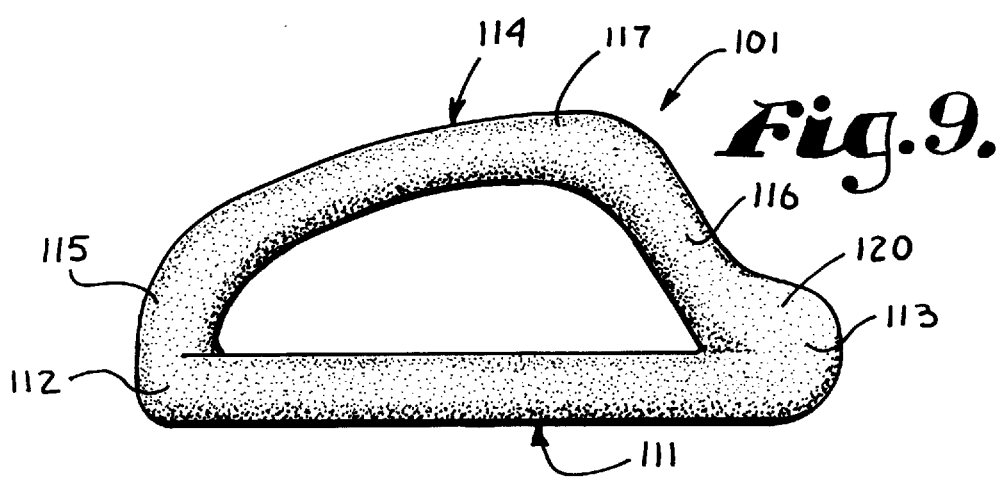
FIG. 9 is a side elevational view of the device of FIG. 7.
Figure 10:
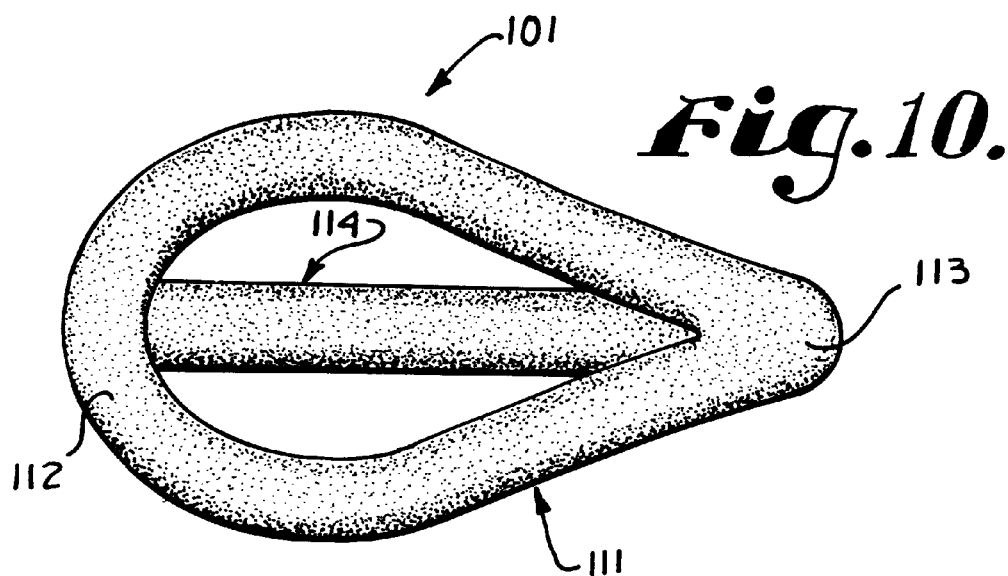
FIG. 10 is a bottom plan view of the apparatus depicted in FIG. 7.
Figure 11:
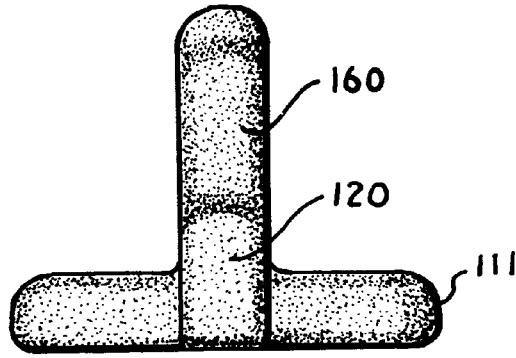
FIG. 11 is a rear elevational view of the apparatus depicted in FIG. 7.
Figure 12:
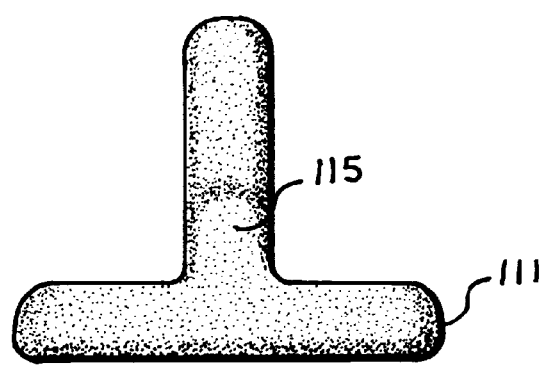
FIG. 12 is a front elevational view of the device of FIG. 7.

In particular, as best shown in FIG. 10, the device 101 includes an open, generally droplet shaped base 111, with an ellipsoid first end 112 and a generally v-shaped second end 113 intercoupled by a support leg 114. As best shown in FIG. 12, the leg 114, extends in a plane orthogonal to the plane of the base 111. The leg 114 includes a first end 115 coupled with the base first end 112 and a second end 116 coupled with the base second end 113. The respective first ends are positioned in a superior orientation during use and the second ends are positioned in an inferior orientation during use. The leg first end 115 is coupled with the base first end 112 in a generally orthogonal relationship. The leg second end 116 is coupled with the base second end 113 in a stepped fashion, so that the base and leg second ends 113 and 116 cooperatively form a graspable indent 120 (FIGS. 9 and 11).

The central portion 117 of the leg 114 has an eccentric elliptical shape which increasingly diverges from the plane of the base 111 as it approaches the inferior second end 116 of the leg 114.

The construction of the device 101 is similar to that previously described for device 1. The base has a length of about 35 to about 115 mm, with a preferred length of about 95 mm and a width at the broadest point of about 25 to about 80 mm, with a preferred width of about 53 mm. The leg extends orthogonal to the plane of the base 111 for a length of about 30 mm to about 60 mm. The material forming the base 111 and leg 114 has a diameter of from about 5 to about 14 mm, with a preferred diameter of about 12.5 mm.

In use, a device 101 is selected in accordance with the dimensions of the vaginal canal 2. The patient grasps the device 101 by the indent 120 and aligns it so that the base 111 faces posteriorly with the first end 112 in a superior orientation and inserts it in a manner substantially similar to the embodiment previously described so that the device 101 is positioned entirely within the canal 2 in remote supporting engagement with the neck of the bladder 5 and the urethra 6.

Thus positioned, the incontinence device 101 of the present embodiment presents a generally D-shaped profile when viewed from the side (FIG. 9), so that the neck of the bladder 5 is supported against the central portion 117 at its highest point, and the urethra 6 is aligned beneath the bladder.

It is to be understood that while certain forms of the present invention have been illustrated and described herein, it is not to be limited to the specific forms or arrangement of parts described and shown. In particular, the configuration of any of the legs described may be employed in either of the embodiments described, or a leg or legs of an infinite variety of shapes may be employed, regardless of whether both ends of the leg are coupled with the base.

What is claimed and desired to be secured by Letters Patent is as follows:

1. An entirely intravaginal device for controlling urinary incontinence by repositioning and supporting a urinary bladder and aligning a urethra, said device comprising:
   a) a base having a first end and a second end, said first end having a superior orientation and said second end having an inferior orientation upon vaginal placement of the device, said base being adapted for engagement with a posterior vaginal wall;
   b) a support leg coupled with said base; and
   c) said support leg having a central portion extending in spaced relation away from said base in an orthogonal plane for engaging an anterior vaginal wall upon vaginal placement and shaped for aligning and supporting the urinary bladder and the urethra.

2. The incontinence device according to claim 1, wherein:
   a) said base has a planar droplet-shaped configuration; and
   b) said base includes a central opening.

3. The incontinence device according to claim 1, wherein:
   a) said leg has an overall D-shaped configuration.

4. The incontinence device according to claim 3, wherein:
   a) said leg includes an indent coupled with said base second end for permitting grasping of the device during insertion and removal.

5. The device according to claim 1, wherein:
   a) said device is constructed of a flexible material for permitting temporary deformation during installation.

6. An entirely intravaginal device for repositioning and supporting a urinary bladder and laterally aligning a urethra, comprising:
   a) a base having a first end and a second end, said first end having a superior orientation and said second end having an inferior orientation upon vaginal placement of the device, said base being adapted for engagement with a posterior vaginal wall;
   b) a pair of elongate parallel support legs coupled with said first end and extending in a predetermined bladder-supporting configuration in orthogonal relationship with the plane of said base for engaging an anterior vaginal wall; and
   c) said support legs having a space therebetween sized to receive and laterally align the urethra upon vaginal placement.

7. The device according to claim 6, wherein:
   a) The base has a planar droplet-shaped configuration, with said first end having an elliptical shape.

8. The device according to claim 6, wherein:
   a) said planar base includes a central opening.

9. The device according to claim 6, wherein:
   a) said legs present an s-shaped profile.

10. The device according to claim 6, wherein:
    a) said device is constructed of a flexible material for permitting temporary deformation during installation.

11. The device according to claim 6, wherein:
    a) said legs each include a superior portion and an inferior portion, said superior portion is curved away from said base and said inferior portion is curved toward said base.

12. The device according to claim 6, wherein:
    a) a portion of each of said support legs overlies said base second end.

13. An entirely intravaginally device for repositioning and supporting a urinary bladder and laterally aligning an associated urethra, comprising:
    a. a base adapted for engagement with a posterior vaginal wall; and
    b. a pair of elongate parallel legs coupled with said base and extending therefrom for engaging an anterior vaginal wall on either side of the urethra for aligning and supporting the urethra between said support legs.

14. The device according to claim 13, wherein:
    a) said base includes a central opening.

15. The device according to claim 13, wherein:
    a) said legs present an s-shaped profile.

16. The device according to claim 13, wherein:
    a) said device is constructed of a flexible material for permitting temporary deformation during installation.

17. The device according to claim 13, wherein:
    a) said legs each include a superior portion and an inferior portion, said superior portion is curved in away from said base and said inferior portion is curved in toward said base.

18. The device according to claim 6, wherein:
    a) a portion of each of said support legs overlies said base second end.

* * * * *